(12) United States Patent
Machida et al.

(10) Patent No.: US 12,334,201 B2
(45) Date of Patent: Jun. 17, 2025

(54) PRESCRIPTION ASSISTANCE DEVICE AND PRESCRIPTION ASSISTANCE METHOD

(71) Applicant: TERUMO KABUSHIKI KAISHA, Tokyo (JP)

(72) Inventors: Yoshihito Machida, Sagamihara (JP); Kei Honda, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 316 days.

(21) Appl. No.: 17/889,653

(22) Filed: Aug. 17, 2022

(65) Prior Publication Data

US 2022/0392599 A1    Dec. 8, 2022

Related U.S. Application Data

(63) Continuation of application No. PCT/JP2021/009084, filed on Mar. 8, 2021.

(30) Foreign Application Priority Data

Mar. 25, 2020  (JP) ................................. 2020-054748

(51) Int. Cl.
*G16H 20/10*    (2018.01)
*G16H 10/60*    (2018.01)

(52) U.S. Cl.
CPC ............. *G16H 20/10* (2018.01); *G16H 10/60* (2018.01)

(58) Field of Classification Search
CPC ............................... G16H 20/10; G16H 10/60
See application file for complete search history.

(56) References Cited

U.S. PATENT DOCUMENTS

| 8,768,719 B2 | 7/2014 | Wehba et al. |
| 2007/0233035 A1 | 10/2007 | Wehba et al. |
| 2007/0233049 A1 | 10/2007 | Wehba et al. |
| 2007/0233050 A1 | 10/2007 | Wehba et al. |

(Continued)

FOREIGN PATENT DOCUMENTS

| JP | 2009531146 A | 9/2009 |
| JP | 2019095960 A | 6/2019 |

(Continued)

OTHER PUBLICATIONS

International Search Report (PCT/ISA/210) with translation and Written Opinion (PCT/ISA/237) mailed on Jun. 1, 2021, by the Japanese Patent Office as the International Searching Authority for International Application No. PCT/JP2021/009084. (10 pages).

(Continued)

*Primary Examiner* — Reginald R Reyes
(74) *Attorney, Agent, or Firm* — Buchanan Ingersoll & Rooney PC (57) ABSTRACT

A prescription assistance device includes a control unit configured to acquire attribute data indicating an attribute of a patient, time series data on a state of the patient, and drug history data indicating a prescription history of a drug for the patient, configured to predict, based on the attribute data, the time series data, and the drug history data, an effect of the drug for each of a plurality of prescription candidates in which combinations of a type, an administration amount, and an administration timing of the drug are different from one another, and configured to present a prediction result to a user.

20 Claims, 6 Drawing Sheets

(56) References Cited

U.S. PATENT DOCUMENTS

| | | |
|---|---|---|
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2011/0313789 A1* | 12/2011 | Kamen ............... G16H 10/60 705/3 |
| 2014/0087999 A1* | 3/2014 | Kaplan ............... C12Q 1/6883 514/5.2 |
| 2019/0035496 A1 | 1/2019 | Netzer et al. |
| 2019/0057762 A1 | 2/2019 | Toyosaki |
| 2019/0156956 A1 | 5/2019 | Tarumi et al. |
| 2021/0043326 A1* | 2/2021 | Janssen ............... G16H 40/63 |

FOREIGN PATENT DOCUMENTS

| | | |
|---|---|---|
| WO | 2017146067 A1 | 8/2017 |
| WO | 2018148365 A1 | 8/2018 |
| WO | 2019/063520 A1 | 4/2019 |

OTHER PUBLICATIONS

English Translations of the International Search Report (Form PCT/ISA/210) and the Written Opinion of the International Searching Authority (Form PCT/ISA/237) issued Jun. 1, 2021, by the Japan Patent Office in corresponding International Application No. PCT/JP2021/009084. (7 pages).

Anonymous: "Acetaminophen and Ibuprofen Dosage Charts", Dec. 31, 2011 (Dec. 31, 2011), XP93063542, Retrieved from the Internet: URL:https://healthonline.washington.edu/sites/default/files/record_pdfs/Acetaminophen-Ibuprofen-Dosage-Charts.pdf. (2 pages).

Anonymous: "Diuretic—Wikipedia", Dec. 12, 2019 (Dec. 12, 2019), XP093063703, Retrieved from the Internet: URL:https://en.wikipedia.org/w/index.php?title=Diuretic&oldid=930435883. (8 pages).

The extended European Search Report issued Jul. 27, 2023, by the European Patent Office in corresponding European Patent Application No. 21776320.0-1126. (15 pages).

* cited by examiner

PRESCRIPTION ASSISTANCE DEVICE AND PRESCRIPTION ASSISTANCE METHOD

CROSS-REFERENCES TO RELATED APPLICATIONS

This application is a continuation of International Application No. PCT/JP2021/009084 filed on Mar. 8, 2021, which claims priority to Japanese Application No. 2020-054748 filed on Mar. 25, 2020, the entire content of both of which is incorporated herein by reference.

TECHNOLOGICAL FIELD

The present disclosure generally relates to a prescription assistance device and a prescription assistance method.

BACKGROUND DISCUSSION

Japanese Patent Application Publication No. 2019-095960 A describes a treatment selection assistance system that predicts, for each treatment unit, an achievement level of a treatment target for a patient, calculates an appropriateness of each treatment unit for the patient, and provides information on a treatment unit suitable for the patient based on the predicted achievement level and the calculated appropriateness.

Treatment on acute heart failure can be performed with a drug such as a diuretic, a cardiotonic, and an infusion. In order to release systemic congestion, a plurality of types of diuretics are combined in accordance with a cardiac function and a renal function, a cardiotonic is used to ensure a urine volume and to help prevent dehydration, and the diuretics, the cardiotonic, and the infusion are adjusted so as to maintain an electrolyte balance, albumin, and the like.

Pathology of patients with heart failure is very diverse. Although a prescription of drugs is determined by an experience of a doctor, it can be difficult to determine the prescription after completely grasping a state of a patient. In addition, when there are a variety of combinations of a type, an administration amount, and an administration timing of the drug as in the treatment of heart failure, it is necessary to determine a complicated prescription. In a system in the related art, it is difficult to assist determination on such a complicated prescription of drugs.

SUMMARY

The present disclosure is to assist determination on a relatively complicated prescription of drugs.

A prescription assistance device as an aspect of the present disclosure includes a processor configured to acquire attribute data indicating an attribute of a patient, time series data on a state of the patient, and drug history data indicating a prescription history of a drug for the patient, configured to predict, based on the attribute data, the time series data, and the drug history data, an effect of the drug for each of a plurality of prescription candidates in which combinations of a type, an administration amount, and an administration timing of the drug are different from one another, and configured to present a prediction result to a user of the effect of the drug for each of the plurality of prescription candidates.

In an embodiment, the time series data includes results of vital measurement on the patient at a plurality of time points, and the processor is configured to predict, as the effect of the drug, results of vital measurement on the patient after drug administration.

In an embodiment, the vital measurement on the patient includes urine volume measurement on the patient.

In an embodiment, the time series data includes results of blood tests on the patient at a plurality of time points, and the processor is configured to predict, as the effect of the drug, results of blood tests on the patient after drug administration.

In an embodiment, the blood test on the patient includes at least one of a cardiac function test, a renal function test, and an electrolyte test on the patient.

In an embodiment, the processor is configured to predict, as the effect of the drug, the number of days until the patient leaves a bed after drug administration.

In an embodiment, the drug includes at least one of a diuretic, a vasodilator, a cardiotonic, a vasopressor, a heart rate controlling drug, an analgesic, and an infusion.

In an embodiment, the processor is configured to receive, from the user, an operation for adjusting at least one of the plurality of prescription candidates.

In an embodiment, the processor is configured to receive, from the user, an operation for selecting any one of the plurality of prescription candidates, and controls, according to the selected prescription candidate, a device configured to administer the drug to the patient.

In an embodiment, the processor is configured to predict the effect of the drug using a trained model to which the attribute data, the time series data, and the drug history data are input and from which the effect of the drug is output.

In an embodiment, when the drug is administered to the patient, the processor is configured to acquire data on the state of the patient at a timing determined for each type of the drug, and to feed the data back to the trained model.

In an embodiment, when a therapeutic intervention different from the drug administration is performed on the patient, the processor is configured to exclude at least a part of the time series data before the therapeutic intervention and to predict the effect of the drug.

In an embodiment, the therapeutic intervention includes at least one of respiratory support and blood circulation support.

A prescription assistance method as an aspect of the present disclosure includes: acquiring, by a prescription assistance device, attribute data indicating an attribute of a patient, time series data on a state of the patient, and drug history data indicating a prescription history of a drug for the patient; predicting, by the prescription assistance device, an effect of the drug for each of a plurality of prescription candidates in which combinations of a type, an administration amount, and an administration timing of the drug are different from one another based on the attribute data, the time series data, and the drug history data; and presenting, by the prescription assistance device, a prediction result to a user of the effect of the drug for each of the plurality of prescription candidates.

A prescription assistance method as another aspect of the present disclosure includes: acquiring attribute data indicating an attribute of a patient, time series data on a state of the patient, and drug history data indicating a prescription history of a drug for the patient; predicting an effect of the drug for a plurality of prescription candidates in which combinations of a type, an administration amount, and an administration timing of the drug are different from one another based on the attribute data, the time series data, and the drug history data; and displaying a prediction result for the effect of the drug for the plurality of prescription candidates in which combinations of the type, the administration amount, and the administration timing of the drug are different from one another based on the attribute data, the time series data, and the drug history data.

According to the present disclosure, it is possible to assist determination on a complicated prescription of drugs.

DETAILED DESCRIPTION

Set forth below with reference to the accompanying drawings is a detailed description of embodiments of a prescription assistance device and a prescription assistance method. Note that since embodiments described below are preferred specific examples of the present disclosure, although various technically preferable limitations are given, the scope of the present disclosure is not limited to the embodiments unless otherwise specified in the following descriptions.

In the drawings, the same or corresponding parts are denoted by the same reference numerals. In the description of the embodiments, the description of the same or corresponding parts will be omitted or simplified as appropriate.

A configuration of a system 10 as an aspect of the present disclosure will be described with reference to FIG. 1.

Figure 1:
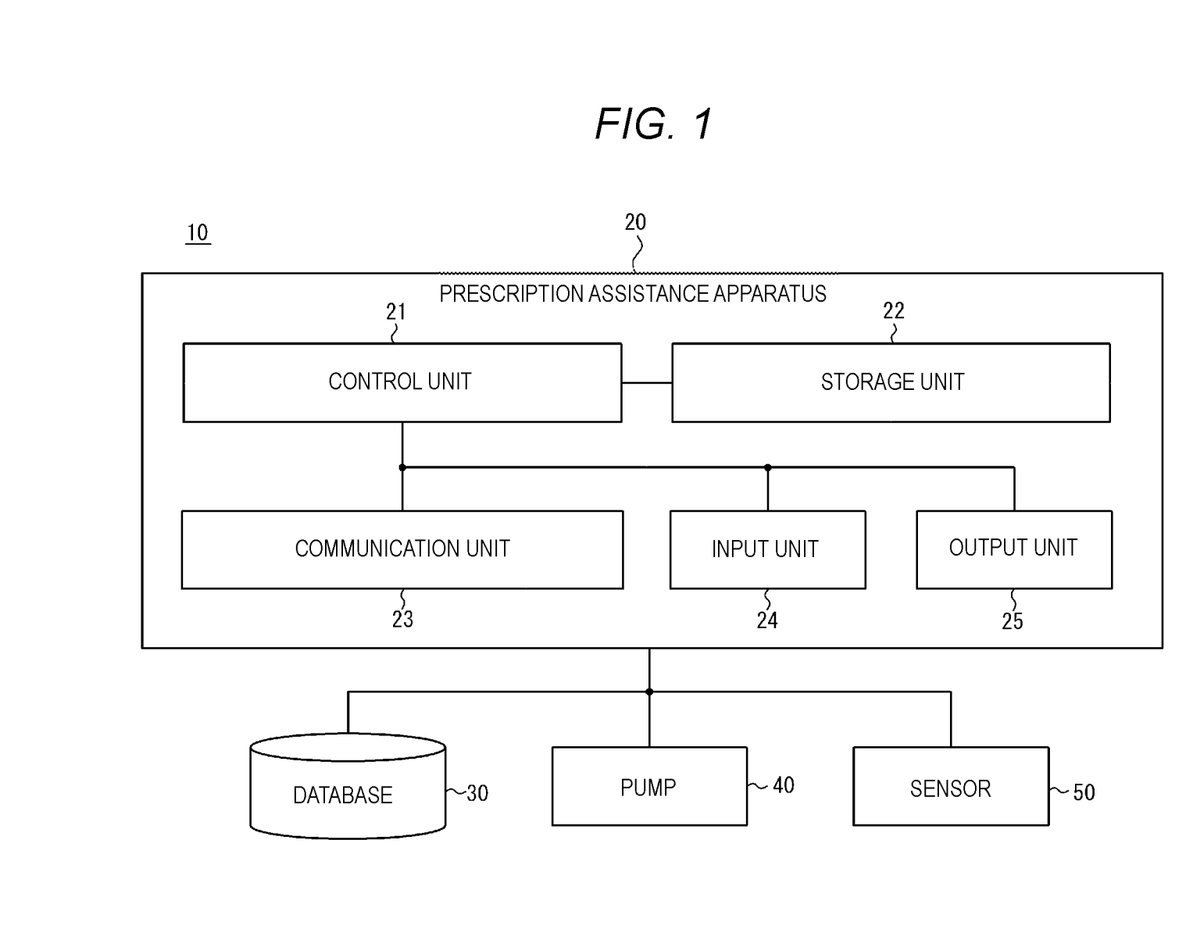
FIG. 1 is a diagram showing a configuration of a system as an aspect of the present disclosure.

The system 10 shown in FIG. 1 includes a prescription assistance device 20, a database 30, a pump 40, and a sensor 50.

The prescription assistance device 20 is communicably connected to the database 30, the pump 40, and the sensor 50 directly or via a network such as a local area network (LAN).

The prescription assistance device 20 can be installed in a hospital as an example, and may be installed in another facility such as a data center. The prescription assistance device 20 can be, for example, a general-purpose computer such as a personal computer (PC) or a server computer, or a dedicated computer.

The database 30 can be installed in a hospital as an example, and may be installed in another facility such as a data center. The database 30 can be, for example, a relational database management system (RDBMS). The database 30 can be separate from the prescription assistance device 20 as an example, or alternatively, may be integrated with the prescription assistance device 20.

The pump 40 may be installed in a hospital. The pump 40 can be, for example, an infusion pump or a syringe pump. The pump 40 may be a smart pump.

The sensor 50 may be installed in a hospital. The sensor 50 can be, for example, a percutaneous oxygen saturation (SpO2) sensor, a heart rate sensor, a blood pressure sensor, a weight scale, a urine volume sensor, a body temperature sensor, a pulse sensor, or a respiration sensor.

A configuration of the prescription assistance device 20 will be described with reference to FIG. 1.

The prescription assistance device 20 can include a control unit 21, a storage unit 22, a communication unit 23, an input unit 24, and an output unit 25.

The control unit 21 can include at least one processor, at least one dedicated circuit, or a combination of at least one processor and at least one dedicated circuit. The processor may be a general-purpose processor such as a central processing unit (CPU) or a graphics processing unit (GPU), or a dedicated processor specialized for specific processing. The dedicated circuit can be, for example, a field-programmable gate array (FPGA) or an application specific integrated circuit (ASIC). The control unit 21 executes processing related to an operation of the prescription assistance device 20 while controlling the units of the prescription assistance device 20.

The storage unit 22 includes at least one semiconductor memory, at least one magnetic memory, at least one optical memory, or a combination of at least two types of the memories. The semiconductor memory can be, for example, a random access memory (RAM) or a read only memory (ROM). The RAM can be, for example, a static random access memory (SRAM) or a dynamic random access memory (DRAM). The ROM can be, for example, an electrically erasable programmable read only memory (EEPROM). The storage unit 22 functions as, for example, a main storage device, an auxiliary storage device, or a cache memory. The storage unit 22 stores data used for the operation of the prescription assistance device 20 and data obtained by the operation of the prescription assistance device 20. The database 30 may be integrated with the prescription assistance device 20 by being constructed in the storage unit 22.

The communication unit 23 includes at least one communication interface. The communication interface can be, for example, a LAN interface. The communication unit 23 receives the data used for the operation of the prescription assistance device 20 and transmits the data obtained by the operation of the prescription assistance device 20.

The input unit 24 includes at least one input interface. The input interface can be, for example, a physical key, a capacitive key, a pointing device, a touch screen provided integrally with a display, or a microphone. The input unit 24 receives an operation for inputting the data used for the operation of the prescription assistance device 20. The input unit 24 may be connected to the prescription assistance device 20 as an external input device instead of being provided in the prescription assistance device 20. For example, any method such as a universal serial bus (USB), a high-definition multimedia interface (HDMI®), or Bluetooth® can be used as a connection method.

The output unit 25 includes at least one output interface. The output interface can be, for example, a display or a speaker. The display can be, for example, a liquid crystal display (LCD) or an organic electro luminescence (EL) display. The output unit 25 outputs the data obtained by the operation of the prescription assistance device 20. The output unit 25 may be connected to the prescription assistance device 20 as an external output device instead of being provided in the prescription assistance device 20. For example, any method such as USB, HDMI, or Bluetooth can be used as a connection method.

A function of the prescription assistance device 20 is implemented by executing a program as an aspect of the present disclosure by a processor corresponding to the control unit 21. That is, the function of the prescription assistance device 20 can be implemented by software. The program causes a computer to function as the prescription assistance device 20 by causing the computer to execute the operation of the prescription assistance device 20. That is, the computer functions as the prescription assistance device 20 by executing the operation of the prescription assistance device 20 according to the program.

The program can be stored in a non-transitory computer-readable medium. The non-transitory computer-readable medium can be, for example, a flash memory, a magnetic recording device, an optical disc, a magneto-optical recording medium, or a ROM. Distribution of the program is executed by, for example, selling, transferring, or lending a portable medium such as secure digital (SD) card, a digital versatile disc (DVD), or a compact disc read only memory (CD-ROM) in which the program is stored. The program may be distributed by storing the program in a storage of a server and transferring the program from the server to another computer. The program may be provided as a program product.

For example, the computer temporarily stores, in a main storage device, the program stored in the portable medium or the program transferred from the server. Then, the computer reads the program stored in the main storage device by the processor, and executes processing according to the read program by the processor. The computer may read the program directly from the portable medium and execute processing according to the program. Each time the program is transferred from the server to the computer, the computer may sequentially execute processing according to the received program. The processing may be executed by a so-called application service provider (ASP) type service in which the function is implemented only by instruction execution and result acquisition without transferring the program from the server to the computer. The program includes information that is provided for processing by an electronic computer and that is treated equivalent to a program. For example, data that is not a direct command to the computer but has a property that defines processing of the computer corresponds to "information that is treated equivalent to a program".

A part or all of the functions of the prescription assistance device 20 may be implemented by a dedicated circuit corresponding to the control unit 21. That is, a part or all of the functions of the prescription assistance device 20 may be implemented by hardware.

Figure 2:
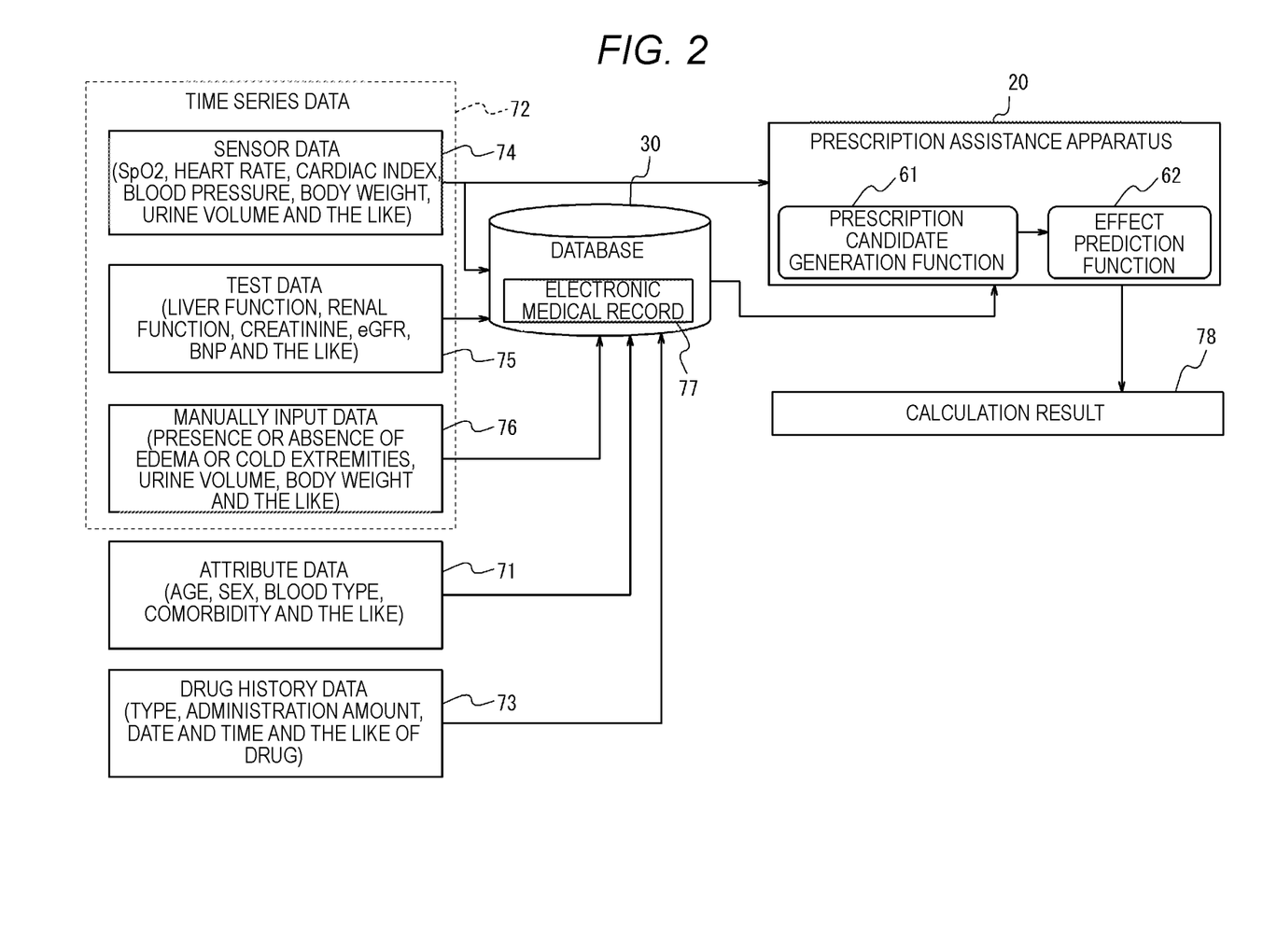
FIG. 2 is a diagram showing functions of the system as an aspect of the present disclosure and a flow of data in the system.

A function of the system 10 as an aspect of the present disclosure and a flow of data in the system 10 will be described with reference to FIG. 2.

The prescription assistance device 20 has a prescription candidate generation function 61 and an effect prediction function 62.

Attribute data 71 indicating an attribute of a patient, time series data 72 on a state of the patient, and drug history data 73 indicating a prescription history of a drug for the patient are registered with the database 30.

The attribute data 71 may be input from another system or manually input. The attribute data 71 can include, for example, data indicating at least one of age, sex, blood type, and comorbidity, as the attribute of the patient.

The time series data 72 includes sensor data 74, test data 75, and manually input data 76. The sensor data 74 can be input from the sensor 50. The sensor data 74 can include, for example, data indicating at least one of SpO2, a heart rate, a cardiac output, a cardiac index, a blood pressure, a body weight, a left ventricular end diastolic pressure, a left ventricular ejection fraction, a central venous pressure, a urine volume, a respiratory rate, a pulmonary artery wedge input pressure, and a body water content, as the state of the patient. The test data 75 may be input, for example, from another system or manually input. The test data 75 can include, for example, data indicating at least one of a liver function, a renal function, creatinine, estimated glomerular filtration rate (eGFR), brain natriuretic peptide (BNP), N-terminal fragment of pro-brain natriuretic peptide (NT-proBNP), hemoglobin, sodium, potassium, blood urea nitrogen (BUN), albumin, and C-reactive protein (CRP), as the state of the patient. The manually input data 76 is manually input. The manually input data 76 can include, for example, data indicating at least one of presence or absence of edema such as leg edema, presence or absence of cold extremities, presence or absence of cyanosis, presence or absence of jugular venous distension, presence or absence of orthopnea, the urine volume, and the body weight, as the state of the patient.

The drug history data 73 can be input from another system or manually input. The drug history data 73 can include data indicating at least one of a type, an administration amount, an administration method, an administration start date and time, and an administration end date and time of the drug.

An electronic medical record 77 is further registered with the database 30. At least one of the attribute data 71, the time series data 72, and the drug history data 73 may be registered as a part of the electronic medical record 77.

The prescription assistance device 20 acquires, from the database 30, the attribute data 71, the time series data 72, the drug history data 73, and the electronic medical record 77. The prescription assistance device 20 may directly acquire, from the sensor 50, the sensor data 74 provided in the time series data 72.

The control unit 21 of the prescription assistance device 20 generates, by the prescription candidate generation function 61, a plurality of prescription candidates in which combinations of a type, an administration amount, and an administration timing of the drug are different from one another. The control unit 21 predicts, by the effect prediction function 62, the effect of the drug for each of the plurality of generated prescription candidates, based on the attribute data 71, the time series data 72, and the drug history data 73. The control unit 21 presents a calculation result 78 which is a prediction result to a user such as a doctor.

According to the above aspects, it is possible to assist determination on a relatively complicated prescription. That is, even when there are a variety of combinations of the type, the administration amount, and the administration timing of the drug are manifold as in treatment on heart failure, it is possible to notify the user of the effect when each combination is applied to the patient and to rather easily determine the prescription.

The prescription candidate generation function 61 may be omitted. For example, instead of generating the plurality of prescription candidates, the control unit 21 of the prescription assistance device 20 may receive an input of a plurality of prescription candidates from the user via the input unit 24 such as a touch screen. Alternatively, the control unit 21 may receive, via the communication unit 23, a plurality of prescription candidates devised by other doctors, which are shared by an external system such as a cloud computing system. Alternatively, the control unit 21 may read a plurality of prescription candidates stored in advance in the storage unit 22.

Hereinafter, several embodiments as specific examples of the aspects shown in FIGS. 1 and 2 will be described with reference to the drawings.

First Embodiment

Figure 3:
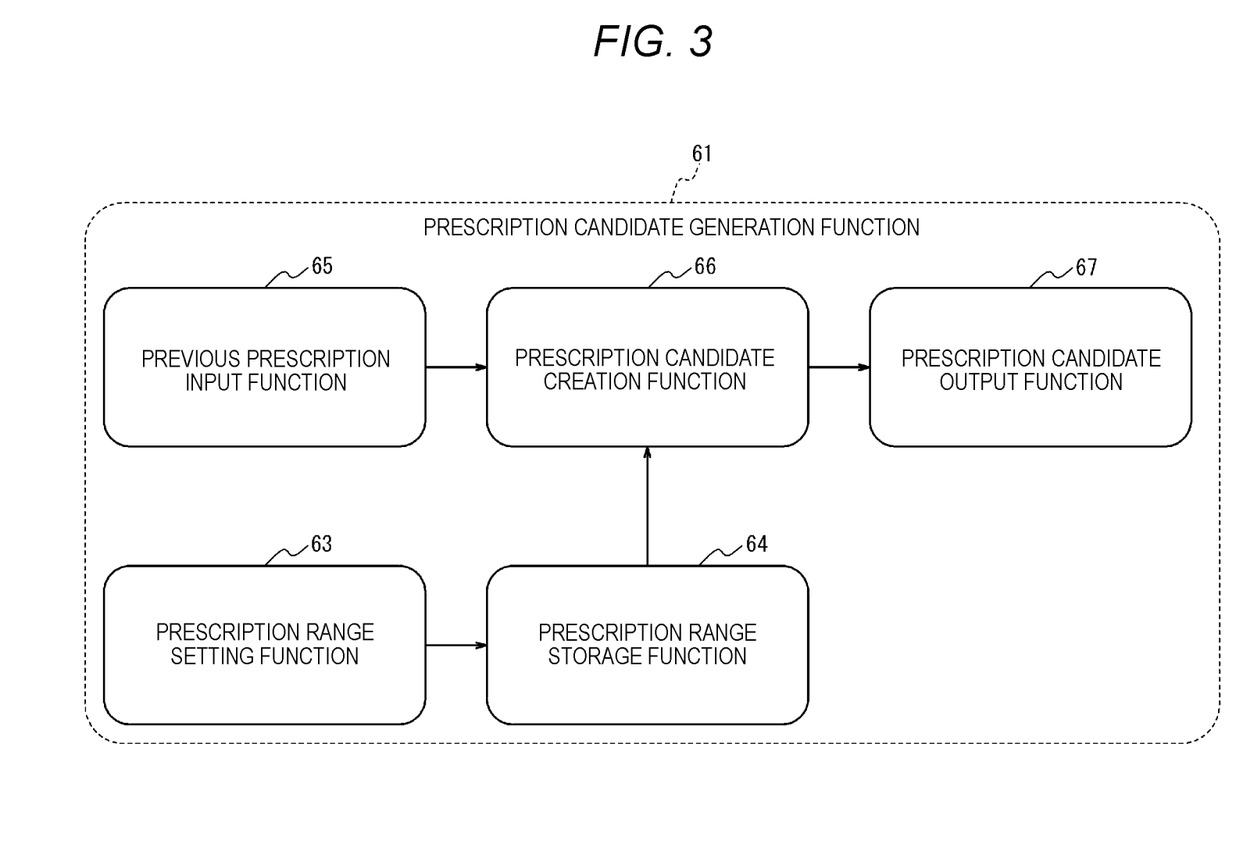
FIG. 3 is a block diagram showing details of a prescription candidate generation function of a prescription assistance device according to a first embodiment.

In the present embodiment, as shown in FIG. 3, the prescription candidate generation function 61 of the prescription assistance device 20 can include a prescription range setting function 63, a prescription range storage function 64, a previous prescription input function 65, a prescription candidate creation function 66, and a prescription candidate output function 67.

Figure 4:
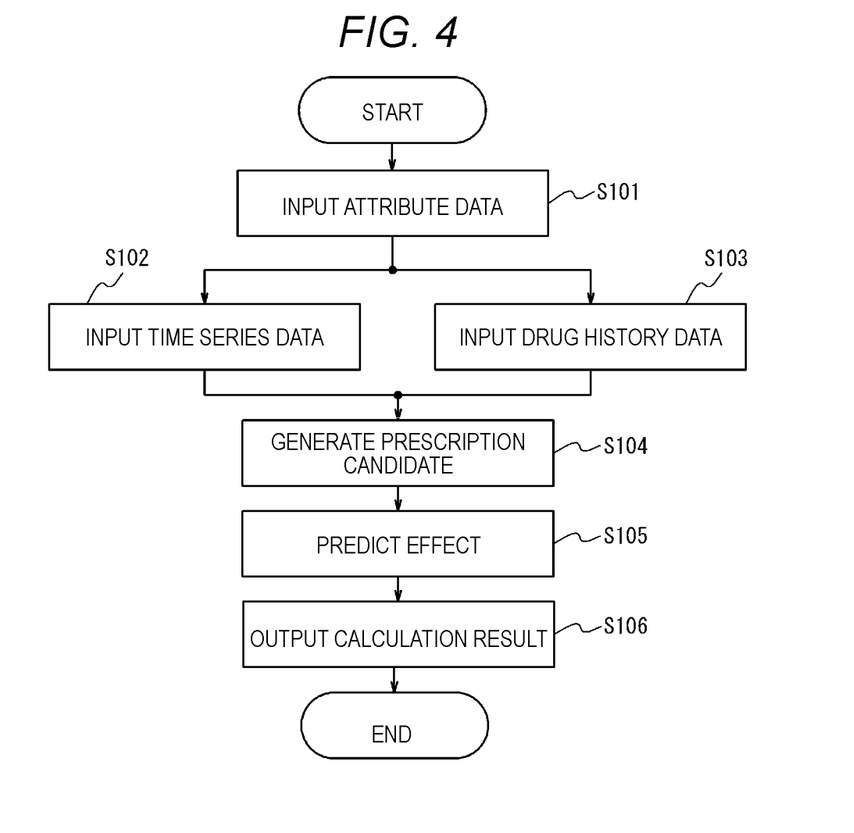
FIG. 4 is a flowchart showing an operation of the prescription assistance device according to the first embodiment.

An operation of the prescription assistance device 20 according to the present embodiment will be described with reference to FIG. 4. The operation corresponds to a prescription assistance method according to the present embodiment.

In S101, the control unit 21 acquires the attribute data 71.

In the present embodiment, the control unit 21 receives an input of the attribute data 71 via the database 30. Specifically, the control unit 21 receives, from the database 30 via the communication unit 23, the attribute data 71 input to the database 30.

As a modification of the present embodiment, the control unit 21 may receive an input of the attribute data 71 from a user via the input unit 24 such as a touch screen.

In S102, the control unit 21 acquires the time series data 72.

In the present embodiment, the control unit 21 receives an input of the time series data 72 via the database 30. Specifically, the control unit 21 receives, from the database 30 via the communication unit 23, the sensor data 74, the test data 75, and the manually input data 76 that are input to the database 30.

As a modification of the present embodiment, the control unit 21 may directly receive an input of the sensor data 74 from the sensor 50. Specifically, the control unit 21 may directly receive, from the sensor 50 via the communication unit 23, the sensor data 74 obtained by the sensor 50. Alternatively, the control unit 21 may receive, from the user via the input unit 24 such as a touch screen, an input of the manually input data 76 and other data that are provided in the time series data 72.

In S103, the control unit 21 acquires the drug history data 73.

In the present embodiment, the control unit 21 receives an input of the drug history data 73 via the database 30. Specifically, the control unit 21 receives, from the database 30 via the communication unit 23, the drug history data 73 input to the database 30.

As a modification of the present embodiment, the control unit 21 may receive an input of the drug history data 73 from the user via the input unit 24 such as a touch screen.

In S104, the control unit 21 generates a plurality of prescription candidates by the prescription candidate generation function 61.

Specifically, the control unit 21 can set, as a prescription range by the prescription range setting function 63, a restriction range of a type, an administration amount, and an administration timing of the drug that may be prescribed. The control unit 21 stores the set prescription range in the storage unit 22 by the prescription range storage function 64.

The control unit 21 receives, from the user via the input unit 24 such as a touch screen by the previous prescription input function 65, an input of a prescription previously applied to a patient. The control unit 21 creates, based on the input previous prescription by the prescription candidate creation function 66, a plurality of prescription candidates by combining the type, the administration amount, and the administration timing of the drug in a plurality of patterns such that the combinations fall within the prescription range stored in the storage unit 22. The control unit 21 outputs the plurality of created prescription candidates by the prescription candidate output function 67.

In the present embodiment, when creating a plurality of prescription candidates, the control unit 21 refers to the attribute data 71 acquired in S101 and adjusts the plurality of prescription candidates to be created according to the attribute of the patient. Alternatively, the control unit 21 may create a plurality of prescription candidates without referring to the attribute data 71.

In the present embodiment, when creating a plurality of prescription candidates, the control unit 21 refers to the time series data 72 acquired in S102 and adjusts the plurality of prescription candidates to be created according to the state of the patient. Alternatively, the control unit 21 may create a plurality of prescription candidates without referring to the time series data 72.

In the present embodiment, when creating a plurality of prescription candidates, the control unit 21 refers to the drug history data 73 acquired in S103 and adjusts the plurality of prescription candidates to be created according to the prescription history of the drug for the patient. Alternatively, the control unit 21 may create a plurality of prescription candidates without referring to the drug history data 73.

As an example, the drug to be prescribed can be a drug used for treatment of heart failure, and specifically can include at least one of a diuretic, a vasodilator, a cardiotonic, a vasopressor, a heart rate controlling drug, an analgesic, and an infusion.

In S105, the control unit 21 predicts, by the effect prediction function 62, an effect of the drug for each of the plurality of prescription candidates generated in S104 based on the attribute data 71 acquired in S101, the time series data 72 acquired in S102, and the drug history data 73 acquired in S103.

Specifically, the control unit 21 can help predict the effect of the drug using a trained model to which the attribute data 71, the time series data 72, and the drug history data 73 are input and from which the effect of the drug is output. The trained model may be constructed by any method, and is constructed by machine learning in the present embodiment. Any method such as recurrent neural network (RNN), support-vector machine (SVM), or random forest can be used as a method of machine learning.

In the present embodiment, the time series data 72 includes results of vital measurement on the patient at a plurality of time points. The control unit 21 predicts, as the effect of the drug, results of vital measurement on the patient after drug administration. As an example, the vital measurement on the patient includes urine volume measurement on the patient.

As an example, the results of the vital measurement on the patient can include a numerical value related to heart failure diagnosis. For example, the results of the vital measurement on the patient can include at least one of SpO2, a heart rate, a cardiac output, a cardiac index, a blood pressure, a body weight, a left ventricular end diastolic pressure, a left ventricular ejection fraction, a central venous pressure, a urine volume, a respiratory rate, a pulmonary artery wedge input pressure, a body water content, a liver function, a renal function, creatinine, eGFR, BNP, NT-proBNP, hemoglobin, sodium, potassium, BUN, albumin, CRP, presence or absence of edema such as leg edema, presence or absence of cold extremities, presence or absence of cyanosis, presence or absence of jugular venous distension, and presence or absence of orthopnea.

In the present embodiment, the time series data 72 can include results of a blood test on the patient at a plurality of time points. The control unit 21 can predict, as the effect of the drug, results of the blood test on the patient after the drug administration. As an example, the blood test on the patient can include at least one of a cardiac function test, a renal function test, and an electrolyte test on the patient.

The control unit 21 may predict, as the effect of the drug, the number of days until the patient leaves a bed after the drug administration.

In S106, the control unit 21 can present, to the user, the calculation result 78 which is a prediction result in S105.

Specifically, the control unit 21 can output the calculation result 78 to the output unit 25, for example, such as a display.

As an example, it is assumed that the influence of drug administration on the renal function of an acute heart failure patient is predicted. In this case, in S102, the sensor data 74 including vital measurement values such as the blood pressure, the heart rate, and a urine flow rate, and the test data 75 including blood test values such as the renal function, the liver function, and albumin are acquired. In S105, a urine flow and creatinine or eGFR are predicted as the effect of the drug. Sodium, chlorine, potassium, blood pressure, heart rate, cardiac output, left ventricular end diastolic pressure, left ventricular ejection fraction, and central venous pressure may be further predicted as the effect of the drug.

For example, in treatment of heart failure, when a confirmation timing for vital, the urine volume, and the like for the doctor to determine the prescription is delayed due to inconvenience of the doctor's work, a timing for switching the prescription may be delayed, and an organ congestion state may be prolonged. According to the example described above, it is possible to make a relatively quick determination and quickly terminate the organ congestion state. It is not necessary to check the vital, the urine volume, and the like, and it is also possible to reduce the burden on the doctor.

For example, it is assumed that the renal function of a certain patient is deteriorated and a fluid overload is predominant. For a patient who does not urinate with a normal amount of the diuretic, when the amount of the diuretic is increased, the urine volume can be quickly ensured, but a large increase in the amount of the diuretic can cause dehydration due to rapid water removal, and there is a concern that the renal function is reduced. The urine volume may be ensured by combining with other diuretics, but in this case, an electrolyte abnormality may occur. In the present embodiment, it is possible to predict a transition in the renal function, the electrolyte, the vital sign, and the like in each prescription candidate, and it can be relatively easy to determine an appropriate amount of the drug and a combination of the drugs.

As a specific example, in a patient with a reduced renal function, generally, furosemide of a small amount of 5 mg or more and 10 mg or less can be intravenously injected initially, and the amount can be increased while confirming a reaction, and continuous administration or the like is also examined. By applying the present embodiment, it is possible to examine how to administer, by any administration method, an appropriate amount of furosemide from an initial stage of the treatment. By applying the present embodiment, it is possible to quickly release congestion while maintaining a renal function, an electrolyte balance, and the like.

As described above, in the present embodiment, the control unit 21 of the prescription assistance device 20 receives an input of the time series data 72 on the patient. The control unit 21 receives an input of the attribute data 71 which is basic data on the patient. The control unit 21 receives an input of the drug history data 73 indicating a prescription history of a drug. The control unit 21 generates a plurality of prescription candidates from the time series data 72, the attribute data 71, and the drug history data 73. The control unit 21 infers an outcome of each prescription candidate on the patient from the time series data 72, the attribute data 71, and the drug history data 73. Specifically, the outcome can be an effect of the drug. As an example, the outcome can be a parameter related to the cardiac function and the renal function of the patient and a parameter related to complications associated with the treatment. The control unit 21 outputs an inference result on the outcome.

In the present embodiment, by selecting a combination of complicated prescriptions from several combinations, it is possible to achieve both simplification of the prescription and improvement of the outcome.

As a modification of the present embodiment, the control unit 21 may receive, from the user, an operation for adjusting at least one of the plurality of prescription candidates. That is, the user may change a plurality of prescription candidates.

As a modification of the present embodiment, when a drug is administered to the patient, the control unit 21 may acquire data on the state of the patient at a timing determined for each type of the drug, and may feed the data back to the trained model used in S105.

As a modification of the present embodiment, when a therapeutic intervention different from drug administration is performed on the patient, the control unit 21 may exclude at least a part of the time series data 72 before the therapeutic intervention and predict the effect of the drug. As an example, the therapeutic intervention can include at least one of respiratory support and blood circulation support. The respiratory support can be performed using, for example, a respirator. The blood circulation support can be performed, for example, as a surgery such as coronary artery bypass grafting.

As a modification of the present embodiment, the control unit 21 may generate a plurality of prescription candidates using a trained model to which the attribute data 71, the time series data 72, and the drug history data 73 are input and from which a plurality of prescription candidates are output. The previous prescription may be included in an input of the trained model.

Second Embodiment

Differences from the first embodiment will be mainly described.

Figure 5:
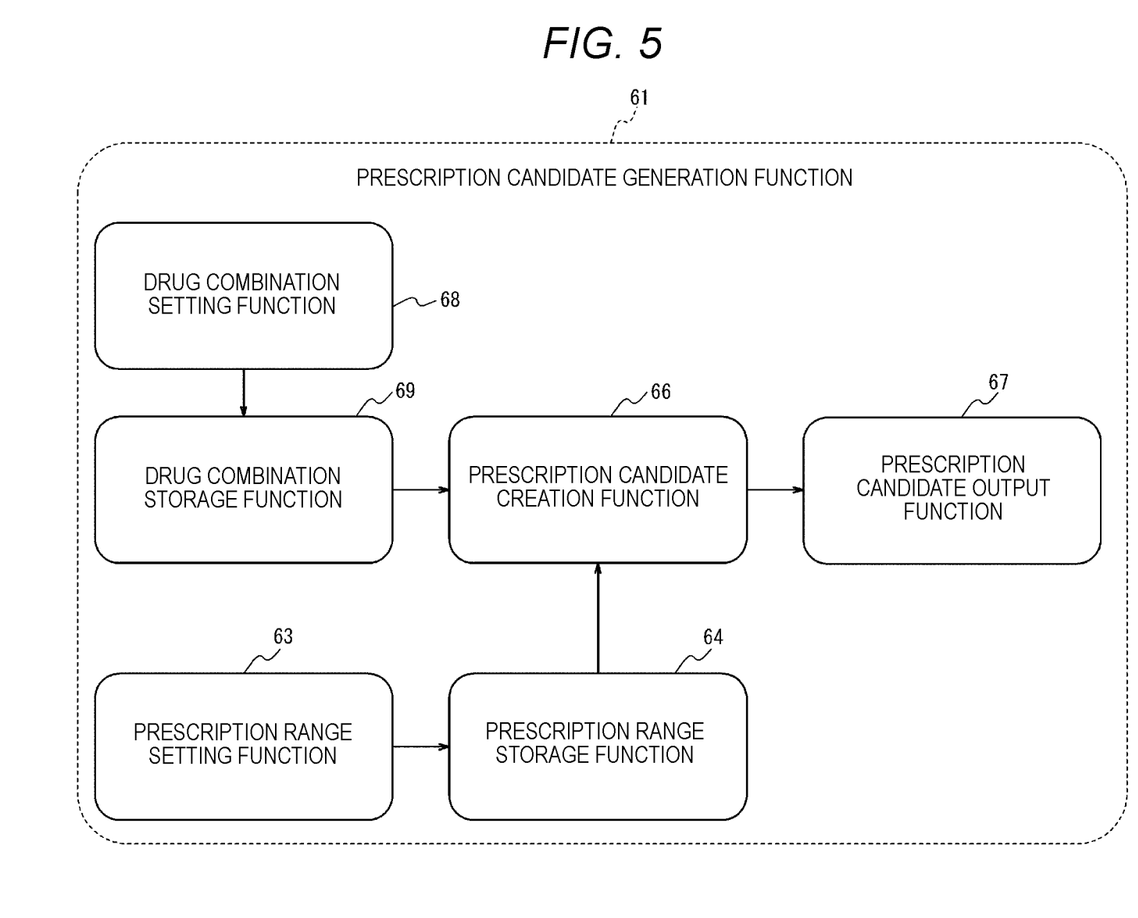
FIG. 5 is a block diagram showing details of a prescription candidate generation function of a prescription assistance device according to a second embodiment.

In the present embodiment, as shown in FIG. 5, the prescription candidate generation function 61 of the prescription assistance device 20 includes, instead of the previous prescription input function 65, a drug combination setting function 68 and a drug combination storage function 69.

Figure 6:
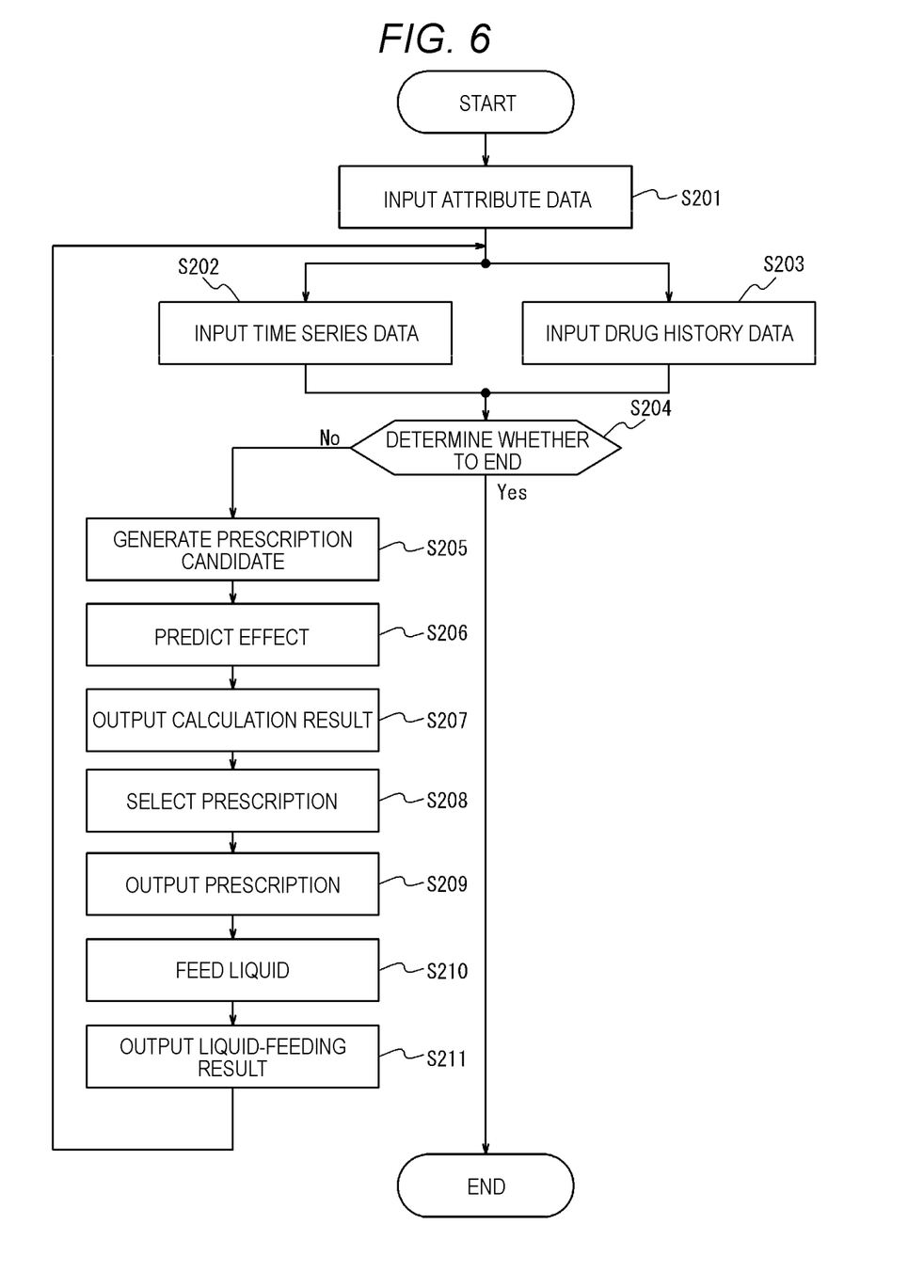
FIG. 6 is a flowchart showing an operation of the prescription assistance device according to the second embodiment.

An operation of the prescription assistance device 20 according to the present embodiment will be described with reference to FIG. 6. The operation corresponds to a prescription assistance method according to the present embodiment.

Since the processing of S201 to S203 is the same as the processing of S101 to S103 in the first embodiment, the description of the processing of S201 to S203 will be omitted.

In S204, when the control unit 21 receives an operation for instructing the end of the processing from a user via the input unit 24 such as a touch screen, the control unit 21 ends the processing. When such an operation is not performed, the processing of S205 is performed.

In S205, the control unit 21 generates a plurality of prescription candidates by the prescription candidate generation function 61.

Specifically, the control unit 21 sets, as a prescription range by the prescription range setting function 63, a restriction range of a type, an administration amount, and an administration timing of the drug that may be prescribed. The control unit 21 stores the set prescription range in the storage unit 22 by the prescription range storage function 64. The control unit 21 receives, by the drug combination setting function 68, an input of one or more combinations of the type, the administration amount, and the administration timing of the drug from the user via the input unit 24 such as a touch screen. The control unit 21 stores, by the drug combination storage function 69, the input combination in the storage unit 22 as a drug combination designated by the user. The control unit 21 creates, by the prescription candidate creation function 66 based on the drug combination designated by the user that is stored in the storage unit 22, a plurality of prescription candidates by combining the type, the administration amount, and the administration timing of the drug in a plurality of patterns such that the combinations fall within the prescription range stored in the storage unit 22. If the drug combination designated by the user falls within the prescription range, the control unit 21 may adopt the drug combination designated by the user as the prescription candidate as it is. The control unit 21 outputs the plurality of created prescription candidates by the prescription candidate output function 67.

Since the processing of S206 and S207 is the same as the processing of S105 and S106 in the first embodiment, the description of S206 and S207 will be omitted.

In S208, the control unit 21 receives, from the user, an operation for selecting one of the plurality of prescription candidates output in S205.

Specifically, the control unit 21 receives, from the user via the input unit 24 such as a touch screen, an operation for selecting one of the plurality of prescription candidates output to the output unit 25 such as a display.

In S209 and S210, the control unit 21 controls a device that administers a drug to a patient in accordance with the prescription candidate selected in S208.

Specifically, the control unit 21 controls the pump 40 such as a smart pump as a device that administers a drug to a patient so that at an administration timing specified by the prescription candidate selected by the user, a drug of a type specified by the prescription candidate is administered to the patient by an administration amount specified by the prescription candidate.

In S211, the control unit 21 presents a drug administration result in S210 to the user.

Specifically, the control unit 21 outputs a drug administration result to the output unit 25 such as a display.

After S211, the processing of S202, S203, and S204 is performed again.

As described above, in the present embodiment, a user can select a prescription according to an inference result on the outcome. Further, the prescribed drug can be fed to the patient according to a prescription selection result by the user. The prescription may be output to the electronic medical record 77 according to the prescription selection result.

As a modification of the present embodiment, a timing at which the control unit 21 acquires the time series data 72 in S202 subsequent to S210 may be set according to the prescription applied in S210. The setting may be manually performed by the user or may be automatically performed by the control unit 21. Further, the set timing may be output, as a time, to the output unit 25 such as a display. When the time series data 72 is not acquired at the time or within a certain period of time from the time, a warning may be output to the output unit 25 such as a display.

As a specific example, it is considered that urine volumes after 15 minutes to 20 minutes and after 2 hours to 4 hours from a time point at which a loop diuretic such as Lasix® is prescribed are predicted, and actual urine volume data after 15 minutes to 20 minutes and after 2 hours to 4 hours is acquired and fed back.

As another specific example, it is considered that a urine volume after 5 minutes from a time point at which a vasopressor such as dobutamine is prescribed is predicted, and actual urine volume data after 5 minutes is acquired and fed back to the control unit 21.

The present disclosure is not limited to the above embodiments. For example, a plurality of blocks described in the block diagram may be integrated, or one block may be divided. Instead of executing the plurality of processes described in the flowchart in time series according to the description, the processes may be executed in parallel or in a different order as necessary or according to a processing capability of the device that executes each process. In addition, modifications can be made without departing from the gist of the present disclosure.

The detailed description above describes embodiments of a prescription assistance device and a prescription assistance method. These disclosed embodiments represent examples of the prescription assistance device and the prescription assistance method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A prescription assistance device comprising:
a processor configured to:
acquire attribute data indicating an attribute of a patient, time series data on a state of the patient, and drug history data indicating a prescription history of a drug for the patient;
generate, receive, or read, a plurality of prescription candidates in which combinations of a type, an administration amount, and an administration timing of the drug are different from one another;
predict, based on the attribute data, the time series data, and the drug history data, an effect of the drug for each of the plurality of prescription candidates in which combinations of a type, an administration amount, and an administration timing of the drug are different from one another;

present a prediction result to a user of the effect of the drug for each of the plurality of prescription candidates via an output interface;

receive, from the user, an operation for selecting one of the plurality of prescription candidates outputted on the output interface via an input interface; and control a pump so as to administer a drug of a type specified by the prescription candidate selected by the user to the patient at an administration amount and an administration timing specified by the prescription candidate selected by the user.

2. The prescription assistance device according to claim 1, wherein
the time series data includes results of vital measurement on the patient at a plurality of time points; and
the processor is configured to:
predict, as the effect of the drug for each of the plurality of prescription candidates, results of vital measurement on the patient after drug administration.

3. The prescription assistance device according to claim 2, wherein the vital measurement on the patient includes urine volume measurement on the patient.

4. The prescription assistance device according to claim 1, wherein
the time series data includes results of a blood test on the patient at a plurality of time points; and
the processor is configured to:
predict, as the effect of the drug for each of the plurality of prescription candidates, results of blood tests on the patient after drug administration.

5. The prescription assistance device according to claim 4, wherein the blood test on the patient includes at least one of a cardiac function test, a renal function test, and an electrolyte test on the patient.

6. The prescription assistance device according to claim 1, wherein the processor is configured to:
predict, as the effect of the drug for each of the plurality of prescription candidates, the number of days until the patient leaves a bed after drug administration.

7. The prescription assistance device according to claim 1, wherein the drug for each of the plurality of prescription candidates includes at least one of a diuretic, a vasodilator, a cardiotonic, a vasopressor, a heart rate controlling drug, an analgesic, and an infusion.

8. The prescription assistance device according to claim 1, wherein the processor is configured to:
receive, from the user, an operation for adjusting at least one of the plurality of prescription candidates.

9. The prescription assistance device according to claim 1, wherein the processor is configured to:
predict the effect of the drug for each of the plurality of prescription candidates using a trained model to which the attribute data, the time series data, and the drug history data are input; and
output the effect of the drug for each of the plurality of prescription candidates from the attribute data, the time series data, and the drug history data input into the trained model.

10. The prescription assistance device according to claim 9, wherein when a drug selected from the plurality of prescription candidates is administered to the patient, the processor is configured to:
acquire data on the state of the patient at a timing determined for each type of the drug; and
feed the acquired data on the state of the patient at the timing determined for each type of the drug to the trained model.

11. The prescription assistance device according to claim 1, wherein when a therapeutic intervention different from the drug administration is performed on the patient, the processor is configured to:
exclude at least a part of the time series data before the therapeutic intervention and predicts the effect of the drug for each of the plurality of prescription candidates.

12. The prescription assistance device according to claim 11, wherein the therapeutic intervention includes at least one of respiratory support and blood circulation support.

13. The prescription assistance device according to claim 1, wherein the processor is configured to adjust the plurality of prescription candidates with reference to at least one of the acquired attribute data, the acquired time series data, and the acquired drug history data.

14. A prescription assistance method comprising:
acquiring, by a prescription assistance device, attribute data indicating an attribute of a patient, time series data on a state of the patient, and drug history data indicating a prescription history of a drug for the patient;
generating, receiving, or reading, by the prescription assistance device, a plurality of prescription candidates in which combinations of a type, an administration amount, and an administration timing of the drug are different from one another;
predicting, by the prescription assistance device, an effect of the drug for each of the plurality of prescription candidates in which combinations of the type, the administration amount, and the administration timing of the drug are different from one another based on the attribute data, the time series data, and the drug history data;
presenting, by the prescription assistance device, a prediction result to a user of the effect of the drug for each of the plurality of prescription candidates via an output interface;
receiving, from the user, an operation for selecting one of the plurality of prescription candidates outputted on the output interface via an input interface; and
controlling, by the prescription assistance device, a pump so as to administer a drug of a type specified by the prescription candidate selected by the user to the patient at an administration amount and an administration timing specified by the prescription candidate selected by the user.

15. The prescription assistance method according to claim 14, further comprising:
adjusting, by a prescription assistance device, the plurality of prescription candidates with reference to at least one of the acquired attribute data, the acquired time series data, and the acquired drug history data.

16. A prescription assistance method on a computer using a processor, the prescription assistance method comprising:
acquiring, by the processor, attribute data indicating an attribute of a patient, time series data on a state of the patient, and drug history data indicating a prescription history of a drug for the patient;
generating, by the processor, a plurality of prescription candidates in which combinations of a type, an administration amount, and an administration timing of the drug are different from one another with reference to at least one of the acquired attribute data, the acquired time series data, and the acquired drug history data;
predicting, by the processor, an effect of the drug for the plurality of prescription candidates in which combinations of the type, the administration amount, and the administration timing of the drug are different from one another based on the attribute data, the time series data, and the drug history data;

displaying a prediction result for the effect of the drug for the plurality of prescription candidates in which combinations of the type, the administration amount, and the administration timing of the drug are different from one another based on the attribute data, the time series data, and the drug history data via an output interface;

receiving, from the user, an operation for selecting one of the plurality of prescription candidates outputted on the output interface via an input interface; and controlling, by the processor, a pump so as to administer a drug of a type specified by the prescription candidate selected by the user to the patient at an administration amount and an administration timing specified by the prescription candidate selected by the user.

17. The prescription assistance method according to claim 16, wherein the time series data includes results of vital measurement on the patient at a plurality of time points, and further comprising:

predicting as the effect of the drug for the plurality of prescription candidates, results of vital measurement on the patient after drug administration.

18. The prescription assistance method according to claim 16, wherein the time series data includes results of a blood test on the patient at a plurality of time points, and further comprising:

predicting, as the effect of the drug for the plurality of prescription candidates, results of blood tests on the patient after drug administration.

19. The prescription assistance method according to claim 16, further comprising:

predicting, as the effect of the drug for the plurality of prescription candidates, the number of days until the patient leaves a bed after drug administration.

20. The prescription assistance method according to claim 16, further comprising:

predicting the effect of the drug for the plurality of prescription candidates using a trained model to which the attribute data, the time series data, and the drug history data are input; and outputting the effect of the drug for the plurality of prescription candidates from the attribute data, the time series data, and the drug history data input into the trained model.

* * * * *